US012485059B2

(12) United States Patent
Cho et al.

(10) Patent No.: US 12,485,059 B2
(45) Date of Patent: Dec. 2, 2025

(54) DRIVING METHOD OF THERMAL MASSAGE DEVICE FOR STRENGTHENING IMMUNITY

(71) Applicant: CERAGEM CO., LTD., Cheonan-si (KR)

(72) Inventors: Il Young Cho, Jeonju-si (KR); Yong son Park, Asan-si (KR); Sang Min Lee, Cheonan-si (KR); Ki Sung Kim, Cheonan-si (KR); Ka Eun Kim, Cheonan-si (KR)

(73) Assignee: CERAGEM CO., LTD., Cheonan-si (KR)

( * ) Notice: Subject to any disclaimer, the term of this patent is extended or adjusted under 35 U.S.C. 154(b) by 1139 days.

(21) Appl. No.: 17/101,262

(22) Filed: Nov. 23, 2020

(65) Prior Publication Data

US 2021/0154088 A1 May 27, 2021

(51) Int. Cl.
*A61H 15/02* (2006.01)
*A61H 15/00* (2006.01)
(Continued)

(52) U.S. Cl.
CPC ............ *A61H 15/02* (2013.01); *A61H 39/06* (2013.01); *A61M 21/02* (2013.01);
(Continued)

(58) Field of Classification Search
CPC .......... A61H 1/00; A61H 1/005; A61H 1/008; A61H 15/0078; A61H 15/02;
(Continued)

(56) References Cited

U.S. PATENT DOCUMENTS 5,076,260 A * 12/1991 Komatsu ............ A61H 23/0236 601/56
6,123,661 A * 9/2000 Fukushima ........... A61M 21/00 600/26
(Continued)

FOREIGN PATENT DOCUMENTS

JP 3087361 U 8/2002
JP 3402723 B2 5/2003
(Continued)

OTHER PUBLICATIONS

Jae Young Cho, English Translation of KR 10-1857555, "U.S. Appl. No. 17/101,262, filed Feb. 5, 2024_KR_101857555_B1_M.pdf", May 14, 2018 (Year: 2018).*
(Continued)

*Primary Examiner* — Tu A Vo
(74) *Attorney, Agent, or Firm* — Knobbe, Martens, Olson & Bear, LLP

(57) ABSTRACT

A method of driving a thermal massage device can include: a pre-stroke step wherein the heating moxibustion device scans the entire spine of the user in order to determine position and shape of the spine of the user and massages the entire spine of the user with a first intensity in order to relax nerves or muscles of the user; a first main stroke step wherein the heating moxibustion device massages the spine while moving according to a first massage pattern for inducing the user's sleep; a second main stroke step wherein the heating moxibustion device massages the spine while moving according to a second massage pattern for maintaining the user's sleep and preparing for sleep escape; and a finish stroke step wherein the heating moxibustion device massages the spine while moving according to a third massage pattern for inducing the user's sleep escape and nerve balance.

10 Claims, 4 Drawing Sheets

(51) Int. Cl.

| | |
|---|---|
| ***A61H 39/06*** | (2006.01) |
| ***A61M 21/00*** | (2006.01) |
| ***A61M 21/02*** | (2006.01) |

(52) U.S. Cl.

CPC ................ *A61H 2015/0014* (2013.01); *A61H 2201/0207* (2013.01); *A61H 2205/081* (2013.01); *A61M 2021/0022* (2013.01); *A61M 2021/0066* (2013.01)

(58) Field of Classification Search

CPC ...... A61H 23/006; A61H 23/02; A61H 39/06; A61H 2015/0014; A61H 2015/0028; A61H 2201/0142; A61H 2201/0207; A61H 2201/0228; A61H 2201/1207; A61H 2201/1623; A61H 2201/1669; A61H 2201/50; A61H 2201/5007; A61H 2201/5035; A61H 2203/0456; A61H 2205/081; A61H 2230/625; A61H 2230/855

See application file for complete search history.

(56) References Cited

U.S. PATENT DOCUMENTS

| | | | | |
|---|---|---|---|---|
| 8,888,808 | B1 | 11/2014 | Park | |
| 10,285,895 | B2 * | 5/2019 | Lee | A61F 7/007 |
| 2007/0083079 | A1 * | 4/2007 | Lee | A61B 5/4806 600/27 |
| 2012/0125337 | A1 * | 5/2012 | Asanoi | A61M 16/026 128/204.23 |
| 2013/0041396 | A1 | 2/2013 | Ryotokuji | |
| 2014/0277300 | A1 * | 9/2014 | Lee | A61B 5/6892 607/96 |
| 2014/0371638 | A1 * | 12/2014 | Lee | A61H 15/0078 601/18 |
| 2016/0015314 | A1 * | 1/2016 | Dusanter | A61B 5/4818 600/301 |
| 2018/0168485 | A1 * | 6/2018 | Chen | A61B 5/4812 |
| 2019/0160253 | A1 * | 5/2019 | Bae | A61H 15/02 |
| 2019/0216680 | A1 * | 7/2019 | Lee | A61H 1/00 |
| 2019/0328609 | A1 | 10/2019 | Park | |
| 2020/0163824 | A1 * | 5/2020 | Kim | A61H 15/0078 |
| 2020/0330322 | A1 * | 10/2020 | Kang | A61H 15/0078 |

FOREIGN PATENT DOCUMENTS

| | | | | | |
|---|---|---|---|---|---|
| JP | 2008-253631 | A | | 10/2008 | |
| KR | 200176650 | Y1 | * | 4/2000 | A61N 5/06 |
| KR | 20000054203 | A | * | 9/2000 | A61H 23/02 |
| KR | 10-2003-0069647 | A | | 8/2003 | |
| KR | 101230665 | B1 | * | 2/2013 | A61H 39/02 |
| KR | 10-1324002 | B1 | | 10/2013 | |
| KR | 101836863 | B1 | * | 3/2018 | A61H 15/02 |
| KR | 101857555 | B1 | * | 5/2018 | |
| KR | 20180075868 | A | * | 7/2018 | A61H 15/0078 |
| KR | 10-1942267 | B1 | | 1/2019 | |
| KR | 10-2014218 | B | | 8/2019 | |
| KR | 102014218 | B1 | * | 8/2019 | A61M 21/02 |

OTHER PUBLICATIONS

Office Action of Korean Patent Application No. 10-2019-0151011—15 pages (Jun. 18, 2021).

Hearing Notice of corresponding Indian Patent Application No. 202014050569 issued on Jan. 8, 2024.

* cited by examiner (a)

| | | | | |
|---|---|---|---|---|
| stage 1 (NREM 1) | stage 2 (NREM 2) | stage 3 (NREM 3) | stage 4 (NREM 4) | stage 5 (REM) |
| 5~15min. | 5~15min. | 5~15min. | 5~15min. | 10min. (1st cycle) |

45 to 85 minutes (b)

DRIVING METHOD OF THERMAL MASSAGE DEVICE FOR STRENGTHENING IMMUNITY

CROSS-REFERENCE TO RELATED APPLICATION

This application claims priority to and the benefit of Korean Patent Application No. 10-2019-0151011, filed on Nov. 22, 2019, the disclosure of which is incorporated herein by reference in its entirety.

TECHNICAL FIELD

The present disclosure relates to a method of driving a thermal massage device for strengthening immunity.

BACKGROUND

A spinal thermal massage device is a device that performs a massage by applying heat stimulation to the spine while a heating moxibustion device moves along the spine of a user.

Such spinal thermal massage device may use electric energy to heat a heating element at a high temperature and induces a heating moxibustion device to emit far infrared radiation in a heated state and at the same time to massage the user's spine, providing a thermal poultice effect and a massage effect.

Despite the high purchase fever of home massage device so far, companies interpret differently how the spinal thermal massage device induces a positive effect on the human body, and in some cases there is no scientific basis.

In particular, a spinal thermal massage device uses a method of delivering stimulation to immune related organs by massaging a specific spine area related to immune function by a heating moxibustion device to improve immunity, but such a method has insufficient theoretical background and description.

The disclosure of this section is to provide background information relating to the invention. Applicant does not admit that any information contained in this section constitutes prior art.

SUMMARY

The present disclosure is directed to providing a method of driving a thermal massage device for strengthening immunity of a user by inducing sleep for a user using a spinal thermal massage device, based on the idea that immunity has a very high correlation with sleep.

Aspects of the present invention provide a method of driving a thermal massage device for strengthening immunity to massage spine of a user while a heating moxibustion device moves in a longitudinal direction of the spine of the user, including: a pre-stroke step wherein the heating moxibustion device scans the entire spine of the user in order to determine position and shape of the spine of the user and massages the entire spine of the user with a first intensity in order to relax nerves or muscles of the user; a first main stroke step wherein the heating moxibustion device massages the spine while moving according to a first massage pattern for inducing the user's sleep; a second main stroke step wherein the heating moxibustion device massages the spine while moving according to a second massage pattern for maintaining the user's sleep and preparing for sleep escape; and a finish stroke step wherein the heating moxibustion device massages the spine while moving according to a third massage pattern for inducing the user's sleep escape and nerve balance.

Here, one sleep cycle may include a first to fourth sleep stage of non-REM sleep and a fifth sleep stage of REM sleep, and the second main stroke step may be a step of massaging until the user's sleep state passes from the second sleep stage to the third sleep stage.

In addition, the first main stroke step may include a step of massaging, by the heating moxibustion device, the spine with a second intensity stronger than the first intensity and a step of massaging, by the heating moxibustion device, a parasympathetic nerve section of the spine with the first intensity.

In addition, the finish stroke step may be a step of massaging, by the heating moxibustion device, the spine with the second intensity, and then massaging with the first intensity.

In addition, the first massage pattern may include Path 1-1 including a sympathetic nerve section, including a parasympathetic section in the middle of the path to maintain nerve balance, and Path 1-2 including a parasympathetic section.

In addition, Path 1-1 may be a path including C1 to L4/L5, L4/L5 to C7/T1, C7/T1 to S3/S4, S3/S4 to T12/L1, T12/L1 to S3/S4, S3/S4 to C7/T1, C7/T1 to T12/L1 and T12/L1 to C1, and Path 1-2 may be a path including C1 to S3/S4, S3/S4 to S1/S2 (2 times of reciprocations), S3/S4 to C1 and C1 to S3/S4.

In addition, in Path 1-1, thermal stimulation points may be located at T4/T5 in a path of C1 to L4/L5, at T6/T7 in a path of L4/L5 to C7/T1, at T10/T11 in a path of C7/T1 to S3/S4, and at L2/L3 in a path of S3/S4 to T12/L1.

In addition, the second massage pattern may include Path 2-1 sequentially including a sympathetic nerve section and a parasympathetic nerve section, and Path 2-2 including cervical vertebrae section to prepare for sleep escape.

In addition, Path 2-1 may be a path including S3/S4 to C7/T1 (2 times of reciprocations), S2/S3 to T6/T7 (2 times of reciprocations), S2/S3 to T8/T9 (2 times of reciprocations), S2/S3 to T5/T6, L3/L4 to C7/T1, C7/T1 to L4/L5 (2 times of reciprocations), and S3/S4 to T12/L1 (2 times of reciprocations), and Path 2-2 may be a path including C7/T1 to C1 (2 times of reciprocations).

In addition, in Path 2-2, a thermal stimulation point may be located at S2/S3 in a path of S3/S4 to T12/L1 (2 times of reciprocations).

In addition, the third massage pattern may include Path 3-1 sequentially including the entire spine and a sympathetic nerve section, and Path 3-2 sequentially including a sympathetic nerve section and the entire spine.

In addition, Path 3-1 may be a path including S3/S4 to C1 (1.5 times of reciprocations) and C1 to T12/L1, and Path 3-2 may be a path including T12/L1 to C7/T1, C7/T1 to S3/S4 and S3/S4 to C1.

According to embodiments of the present invention, immunity of a user may be strengthened by inducing sleep for the user using the spinal thermal massage device.

Advantageous effects of embodiment of the present invention are not limited to the above-described effects, and other effects not mentioned will be clearly understood by those of ordinary skill in the art from the present specification and the accompanying drawings.

BRIEF DESCRIPTION OF THE DRAWINGS

The above and other aspects, features, and advantages of the present invention will become more apparent to those of ordinary skill in the art by describing embodiments thereof in detail with reference to the accompanying drawings, in which.

DESCRIPTION OF SYMBOLS

Figure 1:
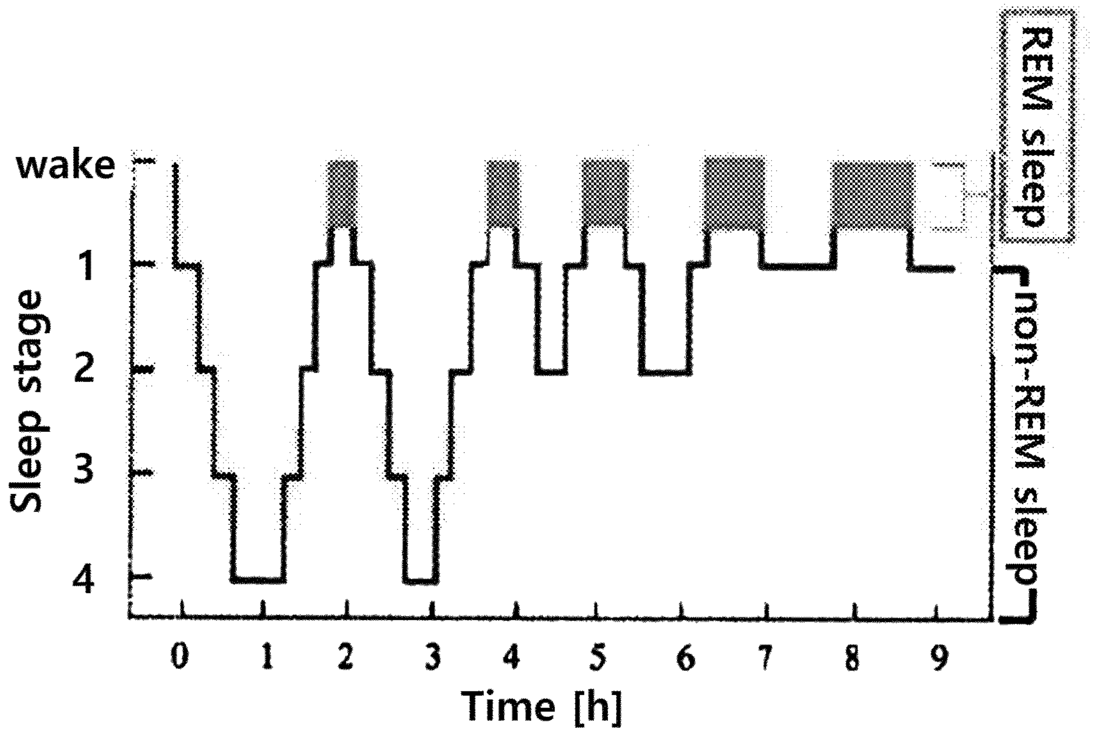
FIG. 1 shows a graph (a) of a person's sleep cycle and a table (b) showing the time required at each sleep phase of the sleep cycle.

100: spinal thermal massage device
110: heating moxibustion device
126: conveying means
140: motor

DETAILED DESCRIPTION OF EMBODIMENTS

Hereinafter, embodiments of the present invention are described in detail with reference to the accompanying drawings. Embodiments of the present invention may be modified into various other forms, and the scope of the present invention should not be construed as being limited to the following embodiments. Embodiments of the present invention are provided to describe the present invention more fully to those skilled in the art. Accordingly, the shape of part of the elements in the drawings is exaggeratedly illustrated to emphasize a clearer description. In addition, terms or words used in the present specification and claims should not be construed as limited to their usual or dictionary definition, and they should be interpreted as a meaning and concept consistent with the technical idea of the present invention based on the principle that inventors may appropriately define the concept of terms in order to describe their own invention in the best way.

Immunity is a very important physiological device for maintaining life that protects our body from external or internal disease risk factors. Therefore, immunity is a very natural topic when talking about almost all diseases. Meanwhile, in relation to immunity, sleep is a very important factor that influences immunity. In particular, it has been reported that elderly people have less immunity than younger people, and one of several reasons for this result may be quality of sleep. That is, the quality of sleep decreases for people of higher age, and thus their immunity decreases.

Accordingly, a method of massage for strengthening immunity according to an embodiment of the present invention is directed to providing a method of driving a thermal massage device for strengthening immunity of a user by inducing sleep for the user using the spinal thermal massage device, based on the idea that immunity has a very high correlation with sleep.

FIG. 1 shows a graph (a) of a person's sleep cycle and a table (b) showing the time required at each sleep phase of the sleep cycle.

Human sleep includes REM sleep in which rapid eye movement occurs during sleep and non-REM (NREM) sleep in which rapid eye movement does not occur. REM sleep accounts for 20-25% of total sleep, and non-REM sleep accounts for 75-80% of total sleep. The non-REM sleep includes a first sleep stage (Stage 1) and a second sleep stage (Stage 2), which are shallow sleep, and a third sleep stage (Stage 3) and a fourth sleep stage (Stage 4), which are deep sleep. Here, REM sleep will be referred to as a fifth sleep stage (Stage 5).

Referring to FIG. 1 (*a*), people generally has a sleep time of 7 to 8 hours, during which non-REM sleep and REM sleep are repeated about 5 times in a cycle of about 90 to 120 minutes. Here, one sleep cycle sequentially goes through the first to fourth sleep stages of non-REM sleep, and in reverse sequentially goes through the third, second, and first sleep stages of non-REM sleep, followed by the fifth sleep stage of REM sleep.

Referring to FIG. 1 (*b*), the first to fourth sleep stages (Stage 1 to Stage 4) of non-REM sleep take about 5 to 15 minutes, respectively, and the fifth sleep stage (Stage 5) of REM sleep takes about 10 minutes. In other words, one sleep cycle takes about 45 to 85 minutes.

The method of massage for strengthening immunity according to an embodiment of the present invention includes massaging a spine of a user by a heating moxibustion device while the heating moxibustion device moves in the longitudinal direction of the user's spine during the time corresponding prior to the third sleep stage (Stage 3) such as 37 to 41 minutes out of the time of one full sleep cycle.

Meanwhile, the optimal temperature for inducing sleep indicates 41 to 42.5 degrees Celsius in the experimental results for the younger people in their 20s to 30s, and 40 to 40.5 degrees Celsius in the experimental results for the elderly people in their 60s to 70s. Since the spinal thermal massage device according to an embodiment of the present invention may be mainly used by the elderly, whose immunity is relatively reduced, in one embodiment, overall temperature of 40 to 40.5 degrees Celsius is maintained during the massage, but it is not limited thereto. In addition, in some sections during the massage, the temperature may be raised or lowered than the above-mentioned temperature in order to induce sleep more effectively.

Figure 2:
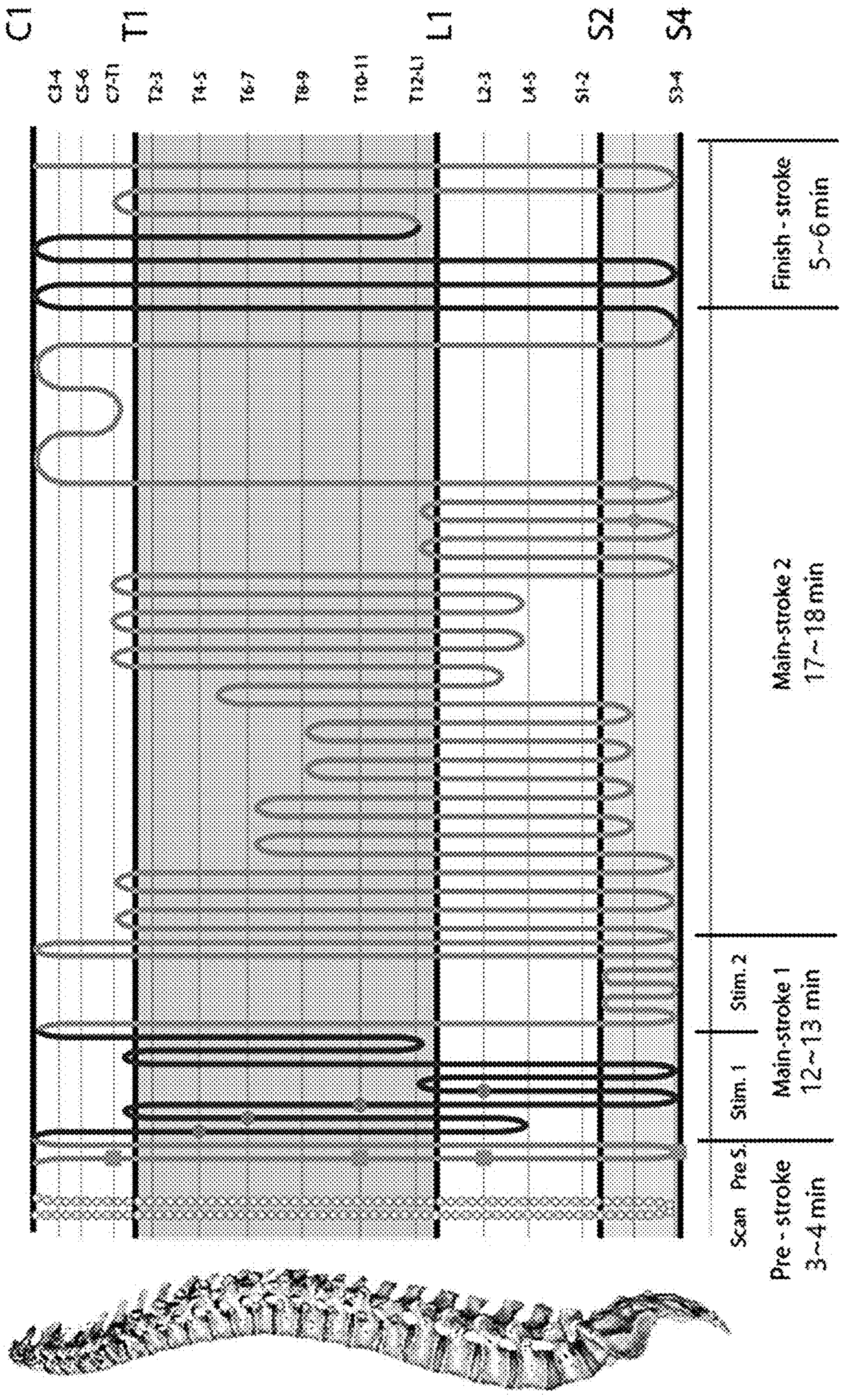
FIG. 2 is a diagram of a massage pattern in a method of driving a thermal massage device for strengthening immunity according to an embodiment of the present invention.

FIG. 2 is a diagram of a massage pattern in a method of driving a thermal massage device for strengthening immunity according to an embodiment of the present invention.

As shown in FIG. 2, the method of driving a thermal massage device according to an embodiment of the present invention includes a pre-stroke step (Pre-stroke), a first main stroke step (Main-stroke 1), a second main stroke step (Main-stroke 2), and a finish stroke step (Finish-stroke).

In the pre-stroke step, the heating moxibustion device massages gently the entire spine of the user in order to prepare for massage or exposure to heat and to minimize specific problems that may be caused by sudden stimulation. Here, potential massage stroke used by Jin Shin Do and effleurage stroke may be used.

Specifically, the pre-stroke step (Pre-stroke) may include a step of scanning, by the heating moxibustion device, the entire spine of a user in order to determine the position and shape of the spine of the user and a step of massaging, by the heating moxibustion device, entire spine with a first intensity in order to relax nerves or muscles of the user prior to the first main stroke (Main-stroke 1).

In embodiments, the pre-stroke step (Pre-stroke) is performed for about 3 to 4 minutes such as 3 minutes and 48 seconds.

In addition, the step of scanning the entire spine of the user is a step for setting a reference point for applying a massage pattern to the spine of the user. For example, the heating moxibustion device is reciprocated once in the longitudinal direction of the user's spine starting from the first bone of the cervical vertebrae to determine the location and shape of the user's spine and to find segmental points between the spine bones. In this case, these segmental points are reference points for applying the massage pattern according to an embodiment of the present invention.

Referring to FIG. 2, the spine is divided into cervical vertebrae (C), thoracic vertebrae (T), lumbar vertebrae (L), and sacral/coccygeal vertebrae (S), and numbered in order of each bone. For example, C1/C2 refers to a segmental point of the first cervical bone and the second cervical bone, and T1/T2 refers to a segmental point of the first thoracic bone and the second thoracic bone. Accordingly, the number of reference points for cervical vertebrae are a total of 7: C1, C1/C2, C2/C3, C3/C4, C4/C5, C5/C6, C6/C7; the number of reference points for thoracic vertebrae are a total of 12: C7/T1, T1/T2, T2/T3, T3/T4, T4/T5, T5/T6, T6/T7, T7/T8, T8/T9, T9/T10, T10/T11, T11/T12; the number of reference points for lumbar vertebrae are a total of 5: T12/L1, L1/L2, L2/L3, L3/L4, L4/L5; and the number of reference points for sacral/coccygeal vertebrae are a total of 4: L5/S1, S1/S2, S2/S3, S3/S4.

Here, the sympathetic nerve section is T1/T2 to L1/L2 and the parasympathetic nerve section is S2/S3 to S5.

After scanning of the user's spine is completed, the heating moxibustion device is reciprocated 2 times in the longitudinal direction of the user's spine with the first intensity, which is a relatively soft intensity, starting from the first bone of the cervical vertebrae (C1) to massage the user's spine to relax verves or muscles of the user. In this case, during the massage process, acupressure is performed at the reference points C7/T1, T10/T11, L2/L3 and S3/S4, respectively, allowing nerves or muscles of the user are relaxed more effectively.

In the first main stroke step (Main-stroke 1), the heating moxibustion device massages the spine while moving according to a first massage pattern for inducing the user's sleep.

Specifically, the first main stroke step (Main-stroke 1) may include a step of massaging, by the heating moxibustion device, the spine with a second intensity stronger than the first intensity (Stim 1) and a step of massaging, by the heating moxibustion device, a parasympathetic nerve section of the spine with the first intensity (Stim 2).

In embodiments, the first main stroke step (Main-stroke 1) is performed for about 12 to 13 minutes such as 12 minutes and 39 seconds.

Figure 3:
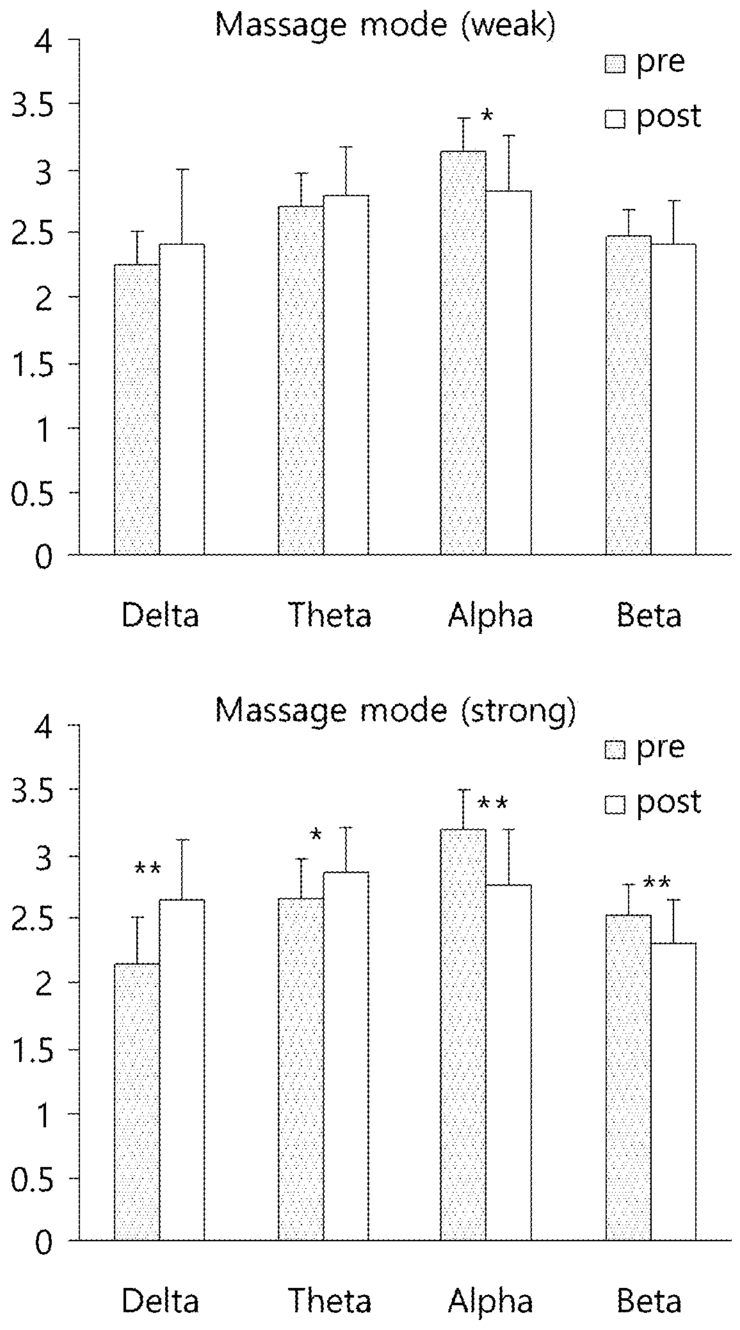
FIG. 3 is a graph comparing the sleep induction effect according to massage intensity.

FIG. 3 is a graph comparing the sleep induction effect according to massage intensity.

The brainwave may include a delta wave, a theta wave, an alpha wave, and a beta wave. Here, the delta wave is a sleep wave that occurs during sleep, the theta wave is a sleepy wave that occurs when falling asleep, and the alpha wave is a stable wave that occurs when the mind and body are at rest. In addition, the beta wave is a stress wave that occurs in situations such as anxiety or tension. Therefore, when a large number of delta waves, theta waves, and alpha waves are generated, the sleep induction effect is high, and when a large number of beta waves are generated, the sleep induction effect is low.

In FIG. 3, brainwaves of a user generated before performing the massage (pre) and after performing the massage (post) were compared.

As shown in FIG. 3, it can be seen that compared to a massage of weaker intensity (massage mode (weak)), delta waves and theta waves were generated more whereas beta waves were generated less in a massage of stronger intensity (massage mode (strong)).

That is, it can be concluded that when massage intensity is stronger, sleep induction effect is higher than when massage intensity is weaker. Accordingly, the method of driving the thermal massage device for strengthening immunity according to an embodiment of the present invention may be able to induce sleep effectively by performing a massage with a relatively strong intensity.

In addition, stimulation of parasympathetic nerve section of the spine, namely, the sacral/coccygeal vertebrae can relax the body, thereby effectively inducing sleep.

Taken together, in the first main stroke step (Main-stroke 1) according to embodiments of the present invention, sleep of a user may be effectively induced by massaging the spine with a relatively strong second intensity, and then massaging the sacral/coccygeal vertebrae (S) associated with the parasympathetic nerve.

In the first main stroke step (Main-stroke 1), the first massage pattern may include a movement path of the heating moxibustion device, the number of reciprocations, a massage intensity, and a thermal stimulation point.

In addition, the first massage pattern may include Path 1-1 and Path 1-2. Here, Path 1-1 may be a path mainly including a sympathetic nerve section, including a parasympathetic section in the middle of the path to maintain nerve balance. In addition, Path 1-2 may be a path including a parasympathetic section.

Specifically, Path 1-1 may be a path including C1 to L4/L5, L4/L5 to C7/T1, C7/T1 to S3/S4, S3/S4 to T12/L1, T12/L1 to S3/S4, S3/S4 to C7/T1, C7/T1 to T12/L1 and T12/L1 to C1, and Path 1-2 may be a path including C1 to S3/S4, S3/S4 to S1/S2 (2 times of reciprocations), S3/S4 to C1 and C1 to S3/S4.

In addition, Path 1-1 may be a path massaged with the second intensity, and Path 1-2 may be a path massaged with the first intensity.

In addition, in Path 1-1, relatively hot thermal stimulation points may be located at T4/T5 in a path of C1 to L4/L5, at T6/T7 in a path of L4/L5 to C7/T1, at T10/T11 in a path of C7/T1 to S3/S4, and at L2/L3 in a path of S3/S4 to T12/L1. Here, T4/T5, T6/T7, T10/T11, and L2/L3 are segmental points associated with gallbladder, pancreas, kidney, and small intestine, respectively, and the overall balance of the internal organs may be maintained by sequentially stimulating these thermal stimulation points.

In the second main stroke step (Main-stroke 2), the heating moxibustion device massages the spine while moving according to a second massage pattern for maintaining the user's sleep and preparing for sleep escape. That is, a massage for maintaining sleep is performed in the first half of the second main stroke step (Main-stroke 2), and a massage for preparing for sleep escape is performed in the second half.

Meanwhile, as described above, when the user enters the third and fourth sleep stages, which are deep sleep, the user may be difficult to wake up, or complain of sleep inertia even if they wake up.

Accordingly, in the second main stroke step (Main-stroke 2), a massage is performed until the user's sleep state passes from the second sleep stage to the third sleep stage. This means that the second main stroke step (Main-stroke 2) may perform a massage while the user's sleep state is in the first and second sleep stages. For example, for the second main stroke step (Main-stroke 2) a massage is performed for about 17 to 18 minutes such as 17 minutes and 15 seconds.

In addition, by massaging the cervical vertebrae (C) section at the end of the second main stroke step (Main-stroke 2), it is possible to prepare for sleep escape, thereby minimizing sleep inertia.

In the second main stroke step (Main-stroke 2), the second massage pattern may include a movement path of the heating moxibustion device, the number of reciprocations, a massage intensity, and a thermal stimulation point.

In addition, the second massage pattern may include Path 2-1 and Path 2-2. Here, Path 2-1 may be a path sequentially including a sympathetic nerve section and a parasympathetic nerve section to maintain sleep, and Path 2-2 may be a path including cervical vertebrae (C) section to prepare for sleep escape.

Specifically, Path 2-1 may be a path including S3/S4 to C7/T1 (2 times of reciprocations), S2/S3 to T6/T7 (2 times of reciprocations), S2/S3 to T8/T9 (2 times of reciprocations), S2/S3 to T5/T6, L3/L4 to C7/T1, C7/T1 to L4/L5 (2 times of reciprocations), and S3/S4 to T12/L1 (2 times of reciprocations), and Path 2-2 may be a path including C7/T1 to C1 (2 times of reciprocations).

In addition, Path 2-1 and Path 2-2 may be paths that are massaged with the first intensity.

In addition, in Path 2-2, a relatively low temperature thermal stimulation point may be located at S2/S3 in a path of S3/S4 to T12/L1 (2 times of reciprocations). Here, S2/S3 is a segmental point associated with a parasympathetic nerve, and maintaining of sleep may be maximized by stimulating this thermal stimulation point.

In the finish stroke step (Finish-stroke), the heating moxibustion device massages the spine while moving according to a third massage pattern for inducing the user's sleep escape and nerve balance.

Specifically, the finish stroke step (Finish-stroke) may be a step of massaging, by the heating moxibustion device, the spine with the second intensity, and then massaging with the first intensity. That is, it may be massaged with the second intensity, which is a relatively strong intensity, and then be massaged with the first intensity, which is a relatively weak intensity, to induce nerve balance.

In this way, in the finish stroke step (Finish-stroke), a massage may be performed with a relatively strong intensity in the first half to realign the muscles to minimize sleep inertia, and a massage may be performed with a relatively weak intensity in the second half to induce nerve balance, thereby normalizing condition so that the user can live natural daily life after massage.

Referring to FIG. 2, in embodiments, a massage for about 5 to 6 minutes such as 5 minutes and 33 seconds is performed in the finish stroke step (Finish-stroke).

The third massage pattern may include a movement path of the heating moxibustion device, the number of reciprocations, and a massage intensity.

In addition, the third massage pattern may include Path 3-1 and Path 3-2. Here, Path 3-1 may be a path sequentially including the entire spine and a sympathetic nerve section, and Path 3-2 may be a path sequentially including a sympathetic nerve section and the entire spine.

In addition, the path of massaging the entire spine among Path 3-1 is a path to realign the muscles by massaging the entire spine with the second intensity, and the path of massaging the sympathetic nerve section among Path 3-1 and Path 3-2 is a path to allow the user to return to daily life by stimulating the sympathetic nerve. And the path of massaging the entire spine among Path 3-2 is a path to induce nerve balance by massaging the entire spine with the first intensity.

Specifically, Path 3-1 may be a path including S3/S4 to C1 (1.5 times of reciprocations) and C1 to T12/L1, and Path 3-2 may be a path including T12/L1 to C7/T1, C7/T1 to S3/S4 and S3/S4 to C1. Here, Path 3-1 may be a path for sleep escape and Path 3-2 may be a path for inducing nerve balance; Path 3-1 may be a path massaged with the second intensity and Path 3-2 may be a path massaged with the first intensity.

Accordingly, the method of driving the thermal massage device for strengthening immunity according to an embodiment of the present invention may be able to strengthen immunity of a user by inducing sleep for the user using the spinal thermal massage device, based on the idea that immunity has a very high correlation with sleep.

Figure 4:
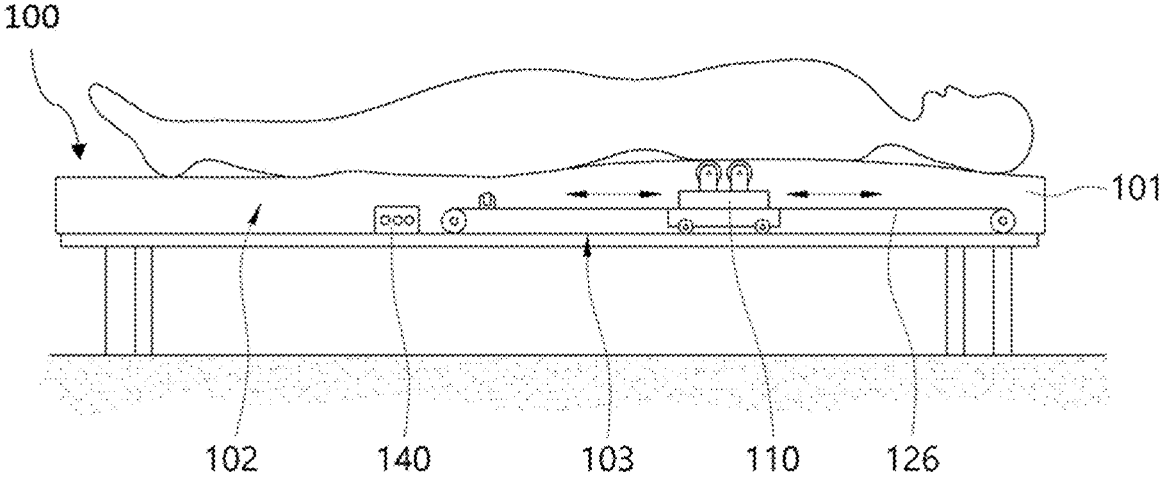
FIG. 4 is a diagram showing a spinal thermal massage device according to an embodiment of the present invention.

FIG. 4 is a diagram showing a spinal thermal massage device according to an embodiment of the present invention.

Hereinafter, a spinal thermal massage device according to an embodiment of the present invention will be described with reference to FIGS. 1 to 4, but the same contents as the above-described method of massage for strengthening immunity will be omitted.

The spinal thermal massage device 100 according to an embodiment of the present invention may include a main mat 101 used for the upper body and spine of the user and an auxiliary mat 102 used for the lower body of the user. In addition, the spinal thermal massage device may include a mounting unit 103 used for mounting and supporting the main mat 101 and the auxiliary mat 102, as necessary.

The spinal thermal massage device 100 is equipped with a heating moxibustion device 110 that massages a user's spine while moving in the longitudinal direction of the user's spine during the time corresponding to one full sleep cycle.

The heating moxibustion device 110 may provide a user with a thermal poultice effect and a massage effect by using high temperature heat and far infrared radiation, etc. generated by using electrical energy supplied from a power supply unit.

The heating moxibustion device 110 may be either a cap type or roller type depending on the shape, but is not limited thereto, and various shapes and structures are possible. Such heating moxibustion device 110 includes a heating unit that generates heat using electric energy and a heat transmission unit heated by the heating unit. Here, the heating unit may include a lamp or electric heater and the heat transmission unit may include a far-infrared radiating material, but they are not limited thereto, and various heating elements or materials and substances that can be heated by heat may be used.

The spinal thermal massage device 100 include a motor 140 and a conveying means 126 so that the heating moxibustion device 110 can reciprocate within the massage device 100 using them. The motor 140 rotates using electric energy, and the conveying means 126 is connected to the motor 140 and transfers rotational force from the rotation of the motor 140 to move the heating moxibustion device 110. The conveying means 126 is coupled to the heating moxibustion device 110 and is used to convey the heating moxibustion device 110 in a forward or backward direction (i.e., in one or the other direction) depending on the normal or reverse rotation of the motor 140. The conveying means 126 may use optionally any of a conveying belt, a conveying chain, and a conveying rope. Of course, the conveying means 126 is not limited thereto, and various means for conveying objects using the driving force of the motor 140 may be used.

The spinal thermal massage device 100 according to an embodiment of the present invention includes a memory in which a massage pattern is stored, and a control unit or controller that controls the conveying means 126 to move the heating moxibustion device 110.

The memory may store the first massage pattern for inducing sleep for a user, the second massage pattern for maintaining sleep and preparing for sleep escape for the user, and the third massage pattern for inducing nerve balance.

Here, the first massage pattern is configured to massage the spine of the user, by the heating moxibustion device 110, with the second intensity stronger than the first intensity, and then to massage the spine section associated with the parasympathetic nerve with the first intensity.

In this way, sleep of the user may be effectively induced by massaging, by the heating moxibustion device 110, the spine of the user with the relatively strong second intensity according to the first massage pattern in the first half, and then massaging the sacral/coccygeal vertebrae (S) associated with the parasympathetic nerve in the second half.

In addition, the second massage pattern is configured to massage until the user's sleep state passes from the second sleep stage to the third sleep stage and is configured to massage while the user's sleep state is in the first and second sleep stages.

In this way, sleep maintenance may be effectively performed by massaging, by the heating moxibustion device 110, according to the second massage pattern, and sleep inertia may be minimized by massaging until the user's sleep state passes from the second sleep stage to the third sleep stage.

Additionally, the third massage pattern may be configured to massage the spine of the user, by the heating moxibustion device 110, with the second intensity, and then to massage with the first intensity.

In this way, the heating moxibustion device 110 may perform a massage with a relatively strong intensity according to the third massage pattern in the first half to realign the muscles to minimize sleep inertia, and may perform a massage with a relatively weak intensity in the second half to induce nerve balance, thereby normalizing condition so that the user can live natural daily life after massage.

The control unit controls the conveying means 126 to move the heating moxibustion device 110 according to the first to third massage patterns stored in the memory.

In addition, the control unit controls the heating moxibustion device 110 to scan the entire spine of the user to determine the position and shape of the spine of the user before the heating moxibustion device 110 massages according to the first pattern. In addition, the control unit controls the conveying means 126 so that the heating moxibustion device 110 massages the entire spine with the first intensity in order to relax the user's nerves or muscles. That is, the control unit controls the control unit 126 so that the heating moxibustion device 110 massages gently the entire spine of the user in order to prepare for massage or exposure to heat and to minimize specific problems that may be caused by sudden stimulation.

Accordingly, the spinal thermal massage device 100 according to an embodiment of the present invention may be able to strengthen immunity of a user by inducing sleep for the user using the spinal thermal massage device, based on the idea that immunity has a very high correlation with sleep.

Embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

The detailed description above is to discuss embodiments of the present invention. In addition, the description above shows and describes embodiments, and the present invention may be used in various other combinations, modifications, and environments. In other words, changes or modifications are possible within the scope of the concept of the invention disclosed in the present specification, the scope equivalent to the disclosed contents, and/or the scope of the skill or knowledge in the art. The embodiments descripted above describes conditions for implementing the technical idea of the present invention, and various changes required in the specific application and use of the present invention are also possible. Therefore, the above-detailed description of the invention is not intended to limit the present invention to the disclosed embodiments. In addition, the attached claims shall be construed as including other embodiments.

What is claimed is:

1. A method of driving a thermal massage device for strengthening immunity to massage the spine of a user while a heating moxibustion device moves in a first direction extending from an upper portion of the spine of the user to a lower portion of the spine of the user or in a second direction opposite to the first direction, comprising:

a pre-stroke step wherein the heating moxibustion device massages the entire spine of the user with a first intensity in order to relax nerves or muscles of the user;

a first main stroke step wherein the heating moxibustion device massages the spine while moving according to a first massage pattern for inducing the user's sleep;

a second main stroke step wherein the heating moxibustion device massages the spine while moving according to a second massage pattern for maintaining the user's sleep and preparing for sleep escape; and a finish stroke step wherein the heating moxibustion device massages the spine while moving according to a third massage pattern for inducing the user's sleep escape and nerve balance, wherein the first massage pattern comprises:

a path 1-1 during which the heating moxibustion device sequentially:

in path (1), moves through a sympathetic nerve section in the first direction, in path (2), moves through the sympathetic nerve section in the second direction without entering a parasympathetic nerve section between path (1) and path (2), in path (3), moves through the sympathetic nerve section in the first direction, in path (4), enters the parasympathetic nerve section in the first direction without re-entering the sympathetic nerve section after path (3), and in path (5), re-enters the sympathetic nerve section, wherein the path 1-1 further includes:

a first thermal stimulation point within path (1), a second thermal stimulation point within path (2) and further along the first direction than the first thermal stimulation point, a third thermal stimulation point within path (3) and further along the first direction than the second thermal stimulation point, and a fourth thermal stimulation point between path (4) and path (5) and further along the first direction than the third thermal stimulation point, such that corresponding internal organs of the user are stimulated in a specific thermal stimulation order, and a path 1-2 during which the heating moxibustion device enters the parasympathetic nerve section, wherein the first main stroke step comprises massaging the spine with a second intensity stronger than the first intensity in the path 1-1, and massaging the spine with the first intensity in the path 1-2 to induce sleep.

2. The method of claim 1, wherein one sleep cycle comprises a first to fourth sleep stage of non-REM sleep and a fifth sleep stage of REM sleep, and in the second main stroke step, a massage is performed until a sleep status of the user passes from the second sleep stage to the third sleep stage.

3. The method of claim 1, wherein the finish stroke step is a step of massaging, by the heating moxibustion device, the spine with the second intensity, and then massaging with the first intensity.

4. The method of claim 1, wherein the path 1-1 is a path comprising C1 to L4/L5, L4/L5 to C7/T1, C7/T1 to S3/S4, S3/S4 to T12/L1, T12/L1 to S3/S4, S3/S4 to C7/T1, C7/T1 to T12/L1 and T12/L1 to C1, and the path 1-2 is a path comprising C1 to S3/S4, S3/S4 to S1/S2 (2 times of reciprocations), S3/S4 to C1 and C1 to S3/S4.

5. The method of claim 4, wherein in the path 1-1, thermal stimulation points are located at T4/T5 in the path of C1 to L4/L5, at T6/T7 in the path of L4/L5 to C7/T1, at T10/T11 in the path of C7/T1 to S3/S4, and at L2/L3 in the path of S3/S4 to T12/L1.

6. The method of claim 5, wherein the second massage pattern comprises a path 2-1 sequentially comprising the sympathetic nerve section and the parasympathetic nerve section, and a path 2-2 comprising cervical vertebrae section to prepare for sleep escape.

7. The method of claim 6, wherein the path 2-1 is a path comprising S3/S4 to C7/T1 (2 times of reciprocations), S2/S3 to T6/T7 (2 times of reciprocations), S2/S3 to T8/T9 (2 times of reciprocations), S2/S3 to T5/T6, L3/L4 to C7/T1, C7/T1 to L4/L5 (2 times of reciprocations), and S3/S4 to T12/L1 (2 times of reciprocations), and the path 2-2 is a path comprising C7/T1 to C1 (2 times of reciprocations).

8. The method of claim 7, wherein in the path 2-2, a thermal stimulation point is located at S2/S3 in the path of S3/S4 to T12/L1 (2 times of reciprocations).

9. The method of claim 8, wherein the third massage pattern comprises a path 3-1 sequentially comprising the entire spine and the sympathetic nerve section, and a path 3-2 sequentially comprising the sympathetic nerve section and the entire spine.

10. The method of claim 9, wherein the path 3-1 is a path comprising S3/S4 to C1 (1.5 times of reciprocations) and C1 to T12/L1, and the path 3-2 is a path comprisingT12/L1 to C7/T1, C7/T1 to S3/S4, and S3/S4 to C1.

* * * * *